United States Patent [19]

Liu

[11] Patent Number: 5,281,265
[45] Date of Patent: Jan. 25, 1994

[54] RESORBABLE SURGICAL CEMENTS

[76] Inventor: Sung-Tsuen Liu, 29 Landing, Laguna Niguel, Calif. 92677

[21] Appl. No.: 830,381

[22] Filed: Feb. 3, 1992

[51] Int. Cl.$^5$ ............................................. C09K 3/00
[52] U.S. Cl. .................................. 106/35; 424/602; 424/696; 501/1; 106/124
[58] Field of Search .......................... 106/35; 501/1

[56] References Cited

U.S. PATENT DOCUMENTS

| | | | |
|---|---|---|---|
| 4,612,053 | 9/1986 | Brown et al. | |
| 4,619,655 | 10/1986 | Hanker et al. | 623/1 |
| 4,668,295 | 5/1987 | BajPai | 106/35 |
| 4,911,759 | 3/1990 | Ohi et al. | 106/111 |
| 5,141,561 | 8/1992 | Ledard et al. | 106/35 |
| 5,149,368 | 9/1992 | Liu | 424/602 |

OTHER PUBLICATIONS

Ohwaki et al, "Experimental Studies on Hydroxyapatite As A Bioactive Cement For Its Application To The Cementless Prostheses", The Third World Biomaterials Congress, Apr. 21-25, 1988, p. 336.

Oonishi et al, "Fully Bioactive Bone Cement Using Tetra-Calcium-Phosphate and Collagen", The 17th Annual Meeting of the Society for Biomaterials, May 1-5, 1991, p. 306.

Sugihara et al, "Surface Bioactive Bone Cement Using Alpha-Tricalcium Phosphate and Collagen", The 17th Annual Meeting of the Society for Biomaterials, May 1-5, 1991, p. 188.

*Primary Examiner*—Helene Klemanski
*Assistant Examiner*—Margaret Einsmann
*Attorney, Agent, or Firm*—Frank J. Uxa

[57] ABSTRACT

A new surgical cement is disclosed. This surgical cement comprises a hardened cement formed from a mixture comprising a cementing component selected from the group consisting of calcium components having a solubility in water at 25° C. in the range of about $0.5 \times 10^{-2}$M to about $20 \times 10^{-2}$M and mixtures thereof; a setting component selected from the group consisting of water soluble salts of polyfunctional carboxylic acids containing 2 to about 10 carbon atoms, water soluble dibasic phosphate salts and mixtures thereof; and water in an amount effective to form a paste from the mixture which paste hardens into said hardened cement which is biocompatible.

20 Claims, No Drawings

RESORBABLE SURGICAL CEMENTS

BACKGROUND OF INVENTION

This invention relates to surgical cements derived from calcium sulfate components in combination with certain setting components. More particularly, the present invention relates to surgical cements formed from calcium sulfate components as cementing components and certain soluble salts as setting components. These cements have been found to have controllable setting times and good manipulation characteristics. Potential applications of these cements include use in or as bone cements, dental cements, bone graft materials, bone substitutes, bone fillers, drug delivery systems and binders for granule forms of bioceramic materials.

In the last two decades, many artificial hard tissue implant materials have been made. Among these, bioglass and bioceramics, such as hydroxyapatite and beta-tricalcium phosphate, have excellent biocompatibility. Most of the bioglass and bioceramics for medical applications are prepared either in granule form or block form. The granule form has mobility problems and relatively poor manipulation characteristics, while the block form is quite brittle and difficult to shape. Many attempts have been made to solve the above-noted problems. Among the materials considered have been Plaster of Paris, collagen, different types of calcium phosphate grout or cement, polylactates and polyacrylate cements. None of these materials is completely acceptable.

The surgeon is most interested in implant materials that can be shaped and hardened in situ. Ideally, a useful surgical cement or binder system for hard tissue applications should have the following characteristics: good biocompatibility, a suitable resorption rate, be moldable at the surgical site, and have a controllable setting time with good setting characteristics.

Most developed surgical cements and binder systems have disadvantages. For example, collagenhydroxyapatite and polylactate-hydroxyapatite composites can only be made as premolded shapes and cannot be molded at the surgical site. Plaster of Paris has reasonable setting characteristics but the resorption rate is too fast. Polyacrylate cement is nonresorbable. Polyacrylic acid-calcium phosphate cement is not resorbable and the setting cement is too acidic. Most of the calcium phosphate grouts or cements are prepared by the reaction of calcium phosphate ceramics with an acidic component. See, for example, Bajpai U.S. Pat. No. 4,668,295. In general, these cements are disadvantageously acidic in nature. These calcium phosphate grouts or cements either lack satisfactory mechanical strength or are resorbed too slowly.

It would clearly be advantageous to provide new surgical cements.

SUMMARY OF THE INVENTION

New surgical cements have been discovered. The present surgical cements are formed from mixtures comprising a cementing component selected from calcium components having a solubility in water at 25° C. in the range of about $0.5 \times 10^{-2}$M (molar in terms of calcium) to about $20 \times 10^{-2}$M and mixtures thereof; water soluble, preferably compatible, salts of polyfunctional carboxylic acids containing 2 to about 10 carbon atoms and/or water soluble, preferably compatible, dibasic phosphate salts; and water in an amount effective to form a paste, preferably a highly viscous paste, from the mixture which hardens into a biocompatible hardened cement. These cements, after setting, preferably have a surface acid/base characteristic which is neutral or slightly alkaline, which is very desirable from a biocompatibility point of view, as opposed to the acid cements, for example, as disclosed in Bajpai U.S. Pat. No. 4,668,295. Since the present cements may be mixed with a variety of other components and have controllable setting times, substantial flexibility in use is achieved, for example, allowing the medical technician to apply this mixture in paste form in situ or to premold the paste, e.g., in the form of an implant.

The present invention permits manipulation of a moldable cementing paste having a reasonable, preferably controllable, setting time at the surgical site for hard tissue replacement. It can also be prepared in premolded shapes. It is important that the final surgical cements, and preferably each of the components of the precursor mixture (in particular, if the cement is to be set or hardened in situ), be biocompatible.

To at least assist in controlling the setting behavior or time and mechanical strength of the present cements, strength enhancing components can be included. The bioresorption rate of these cements can be controlled by adding inert resorbable or non-resorbable fillers. For medical applications, the present surgical cements can be used alone or as a binder system for granules of bioceramics or bioglass.

In summary, the present cements have neutral or slightly alkaline surface characteristics, good biocompatibility, good bioresorbability, workable and preferably controllable setting times, relatively strong mechanical strength and good manipulation characteristics. The cements of the present invention can be used in or as hard tissue replacement materials for orthopedic, dental, maxillofacial and cranial facial surgical applications.

DETAILED DESCRIPTION OF THE INVENTION

The presently useful cementing components are selected from calcium components, for example, calcium salts, which have a solubility in water (pure water) at 25° C. in the range of about $0.5 \times 10^{-2}$M to about $20 \times 10^{-2}$M, preferably about $0.8 \times 10^{-2}$M to about $5 \times 10^{-2}$M. Mixtures of such calcium components may also used. Examples of useful calcium components includes calcium salts of acids, such as calcium sulfate, calcium succinate, calcium malate, calcium malonate, calcium maleate, hydrates of such salts and mixtures thereof. In one embodiment of the present invention, the interaction of the calcium-containing cementing component and the setting component produces a calciumcontaining entity which has reduced solubility in water relative to the calcium-containing cementing component. Particularly useful cementing components are selected from calcium sulfate, calcium sulfate hydrates, calcium sulfate-containing ceramics and mixtures thereof.

There are at least three types of calcium sulfate salts which can be used as the present cementing components. These are calcium sulfate dihydrate, calcium sulfate hemihydrate and anhydrous calcium sulfate. In a pure water system, the solubility of these different types of calcium sulfate ranges from about $1.0 \times 10^{-2}$M to about $4.0 \times 10^{-2}$M at 25° C. Among these calcium sulfate salts, calcium sulfate hemihydrate has a solubility which is much higher than that of calcium sulfate dihydrate. Plaster of Paris is calcium sulfate hemihydrate. When Plaster of Paris is mixed with water, it will dissolve and recrystallize to form gypsum cement which is mainly calcium sulfate dihydrate. Because of its relatively high solubility, gypsum cement resorbs quite fast. In addition, gypsum cement does not by itself form sufficiently cohesive or adhesive pastes.

The cementing component may further be selected from calcium sulfate-containing ceramics. Such ceramics should be such as to permit the desired interaction between the cementing component and the setting component during paste hardening. In fact, any calcium sulfate-containing component which permits this desired interaction is acceptable for use in the present invention. Among the useful calcium sulfatecontaining ceramics are calcium sulfate-calcium alkali (such as sodium, potassium and the like) phosphate mixed ceramics, and the like and mixtures thereof.

The calcium sulfate-containing component preferably comprises at least about 25%, more preferably at least about 30%, by weight of the mixture from which the cement is derived.

The present invention uses water soluble, preferably neutral, salts of polyfunctional carboxylic acids containing 2 to about 10 carbon atoms, preferably citrates, and/or water soluble dibasic phosphate salts as setting components. The polyfunctional carboxylic acids the salts of which are used in the present invention may be saturated or unsaturated. Representative examples of these acids include citric acid, alpha-ketoglutaric acid, pyruvic acid, oxalic acid, tartaric acid, succinic acid, fumaric acid, malic acid, oxalacetic acid, etc. The preferred salts are citrates.

The cation or cations associated with the salt or salts used as setting components should be such as to be biocompatible and not to inhibit or restrict the water solubility of the salt. Examples of useful cations include alkali metal ions, such as sodium, potassium and the like ions, alkaline earth metal ions, such as calcium ions, magnesium ions and the like ions, ferrous ions, ferric ions and the like ions and mixtures thereof.

Examples of useful dibasic phosphate salts include $Na_2HPO_4$, $K_2HPO_4$, $MgHPO_4$, $(NH_4)_2HPO_4$, and the like and mixtures thereof.

The setting components are preferably soluble citrate salts. Examples include sodium citrate, ammonium citrate, potassium citrate, magnesium citrate, any other water soluble and compatible alkali and alkaline earth citrate salts, ferric citrate, ferrous citrate and the like and mixtures thereof. These soluble citrate salts can be used alone, but are advantageously used in any combination with strength enhancing components which together with the setting component are effective to control the setting time of the paste and the mechanical strength of the hardened cement.

Any component effective to facilitate the control of the setting time of the paste and/or the mechanical strength of the hardened cement may be employed as a strength enhancing component. The preferred strength enhancing components are selected from soluble tartrates, soluble dibasic phosphate salts and mixtures thereof. Such components may be useful themselves are setting components, but find particularly attractive usefulness as strength enhancing components when used in conjunction with citrates.

Suitable strength enhancing components include, for example, compatible dibasic ammonium phosphate, dibasic alkali phosphates, dibasic alkaline earth phosphates, ammonium tartrate, alkali tartrate and the like and mixtures thereof. Particularly useful strength enhancing components include $Na_2HPO_4$, $K_2HPO_4$, $MgHPO_4$, $(NH_4)_2HPO_4$, $Na_2$ tartrate, $K_2$ tartrate, NaK tartrate, ammonium tartrate and mixtures thereof. The preferred weight ratio of strength enhancing component to setting component is in the range of about 0.1 to about 2 or about 3 or higher.

Without wishing to limit the invention to any particular theory of operation, the following is believed to occur when the mixture is made from calcium sulfate powder as the cementing component and a soluble neutral citrate as the setting component. When calcium sulfate powder is mixed with a soluble neutral citrate in water, the calcium sulfate salt dissolves to provide calcium ion. This calcium ion reacts or otherwise interacts with citrate ion to form a less soluble calcium citrate salt for the cement formation.

The precursor mixtures of the present invention preferably contain about 100 weight parts to about 500 weight parts of cementing component per 100 weight parts of setting component.

The cementing component used in the present invention can be in the form of particles, such as in the granule form or the powder form. Particle sizes preferably are within the range of about 3 microns to about 200 microns or about 400 microns. For the granule form, particle size is more preferably between about 40 mesh to about 80 mesh. Since the cement formation is believed to involve the dissolution of calcium sulfate and the recrystallization of a less soluble salt, the setting time is a function of the dissolution rate of calcium sulfate. This, in turn, depends on the type and particle size of the calcium sulfate-containing component used. Other factors affecting the setting rate are the amount of water used, and the type of the setting component used.

The surgical cements of the present invention can incorporate biocompatible fillers. Such fillers can be bioresorbable or non-resorbable. The fillers included are preferably substantially inert with respect to the interaction between the cementing component and the setting component during hardening. Such fillers include, for example, calcium oxide, magnesium oxide, calcium fluoride, calcium carbonate, collagen, alpha-tricalcium phosphate, beta-tricalcium phosphate, hydroxyapatite, calcium phosphate apatite, bioglass and other calcium phosphate-containing ceramics and the like and mixtures thereof. The weight ratio of the fillers to the cementing components can be up to about 4 to 1. These fillers can be in the form of particles, such as either granules or powder, which preferably have particle sizes in the range of about 3 microns to about 200 microns or about 400 microns.

In the present invention, any two or all of the cementing components, fillers and setting components can be premixed. To form cement, the premixed material, e.g., powder, comprising all three types of material is added to the desired amount of water, for example, in the form of a saline solution, to form a paste. This paste becomes viscous and adhesive or cohesive. After a certain time, the paste sets and hardens. Alternatively, the setting components are mixed with water first. The cementing components and fillers are then mixed with this aqueous mixture to form a paste. In such case, if the setting component is able to dissolve completely in water, a setting solution can be prepared by dissolving the setting component first. The premixed cementing components and fillers are then pasted with the setting solution.

In general, the setting time of the present cements can be easily controlled, for example, so that the paste hardens or sets in about 20 minutes or less after the paste, for example, the viscous and cohesive paste, is formed. Beside controllable setting times, the present cements have near neutral or slightly alkaline (pH) surface characteristics. In addition, the composition of the cements can be changed over a relatively wide range so as to provide the flexibility and advantages of controlling the resorption rate.

The cements of the present invention can be used in orthopedic, maxillofacial and cranial facial surgical applications and in dental applications. These include 1) a hard tissue replacement material such as bone graft, bone defect filler or bone replacement, 2) ridge augmentation, 3) bone fracture fixation, 4) gluing cement for dentistry and orthopedic surgery, 5) root cement, 6) jaw repair, 7) bone wax substitute and 8) drug release systems. Antibiotic (preferably up to about 20% by weight of the cement) and bone growth proteins (preferably up to 10% by weight of the cement) can be released by the cement of this invention.

For convenient application, the cement of the present invention can be prepared as a paste first. The paste can be introduced into the bone defects or implantation site before it becomes hardened. Alternately, the cement can be premolded to any shape before use. For example, in the drug release system, the required amount of drug may be mixed with the cementing component, the setting component, and optionally the filler, and water to form a paste. After setting, the hardened cement is then dried and broken into suitable sized particles, e.g., granules. These dried cementing particles, which contain the drug, can then be stored before use.

The invention is illustrated in more detail in the following, non limiting examples.

EXAMPLE 1

Calcium sulfate dihydrate of particle size passing through 100 mesh was used. 2 g of calcium sulfate dihydrate was mixed with 0.5 g of potassium citrate. This mixed powder was then mixed with 0.6 ml deionized water and stirred with a spatula. After mixing, the paste became viscous and cohesive. The paste became hardened and set about 2 minutes after mixing. After aging in a water environment, this setting cement maintained its integrity and did not disintegrate.

EXAMPLE 2

2 g of potassium citrate was mixed with 0.7 ml deionized water. 2 g of calcium sulfate dihydrate was then pasted with the potassium-water mixture. The paste was stirred with a spatula. This paste became very viscous. The paste started to harden and set about 7 minutes after mixing.

EXAMPLE 3

2 g of calcium sulfate dihydrate, 0.3 g of ammonium monohydrogen phosphate (($NH_4$)$_2HPO_4$), and 0.7 g of potassium citrate were mixed. This mixed powder was then pasted with 0.7 ml of deionized water to form a sticky paste. This paste became hardened and set about 8 minutes after mixing. This hardened cement showed no signs of disintegration after being aged in water for more than 24 hours.

EXAMPLE 4

2 g of calcium sulfate dihydrate, 0.3 g of ferric ammonium citrate and 1.0 g of potassium citrate was mixed. The mixed powder was then pasted with 0.7 ml of water. The paste became viscous and hardened about 5 minutes after mixing. After aging in water, the hardened cement did not disintegrate and the soaking water showed only a slight pale green color indicating that most of the ferric ion was still retained in the cement.

EXAMPLE 5

2 g of calcium sulfate dihydrate and 1.0 g of NaK tartrate were mixed. The mixture was then pasted with 0.8 ml deionized water. The paste set in less than one minute after mixing. The above setting component was replaced with 0.5 g NaK tartrate and 0.5 potassium citrate. This paste was viscous and set about 8 minutes after mixing. The setting cements did not disintegrate in aqueous environments. This clearly indicates that the addition of other materials which may also involve chemical reaction in cement formation can change the setting time and the manipulation characteristics of the cement precursor paste.

Table 1 sets forth the results of all the examples.

TABLE 1[(1)]

| Example No. | Setting Component, (g) | Strength Enhancing Component, (g) | $H_2O$ (ml) | Setting Time, (Min) |
|---|---|---|---|---|
| 1 | 0.5 g K citrate | 0 | 0.6 | 2 |
| 2 | 2.0 g K citrate | 0 | 0.7 | 7 |
| 3 | 0.7 g K citrate | 0.3 g ($NH_4$)$_2HPO_4$ | 0.7 | 8 |
| 4 | 1.0 g K citrate 0.7 g ferric ammonium citrate | | | |
| 5 | 0 | 1.0 g NaK tartrate | 0.8 | <1 |
| 5 | 0.5 g K citrate | 0.5 g NaK tartrate | 0.8 | 8 |
| 6 | 0.5 g Na citrate | 0.5 g $K_2HPO_4$ | 0.8 | 5 |
| 7 | 0.5 g K citrate | 0.5 g $K_2HPO_4$ | 0.7 | <1 |
| 8 | 0.7 g K citrate | 0.3 g $K_2HPO_4$ | 0.7 | 7 |
| 9 | 0.8 g K citrate | 0.2 g $Na_2HPO_4$ | 0.7 | 5 |
| 10 | 0 | 0.5 g ($NH_4$)$_2HPO_4$ | 0.6 | 1.5 |

[(1)]Each of these tests used 2 g of calcium sulfate dihydrate as the cementing component.

In general, the setting rate depends on the type, crystal morphology and particle size of the calcium-containing component used as the cementing component. In addition, the amount of water, the type and concentration of the setting component, and the type and concentration of the strength enhancing component, if any, can also show significant effects on the setting rate. The present surgical cements have workable (reasonable) and controllable setting times, are biocompatible, are easily manipulated, may be formed in situ or in premolded shapes, and have a wide variety of applications.

While this invention has been described with respect to various specific examples and embodiments, it is to be understood that the invention is not limited thereto and that it can be variously practiced within the scope of the following claims.

What is claimed is:

1. A surgical cement for use in medical applications such as orthopedic and maxillofacial surgeries and dental applications comprising a hardened cement formed from a mixture comprising a cementing component selected from the group consisting of calcium sulfate-containing components, calcium succinate, calcium malate, calcium malonate, calcium maleate, hydrates thereof and mixtures thereof, said cementing component having a solubility in water at 25° C. in the range of about $0.5 \times 10^{-2}$ M to about $20 \times 10^{-2}$ M; a setting component selected from the group consisting of water soluble, neutral salts of polyfunctional carboxylic acids containing 2 to about 10 carbon atoms, water soluble dibasic phosphate salts and mixtures thereof; and water in an amount effective to form a paste from said mixture which paste hardens into said hardened cement which is biocompatible, provided that the weight ratio of said cementing component to said setting component in said mixture is in the range of about 1:1 to about 5:1.

2. The surgical cement of claim 1 wherein said hardened cement has a surface which is substantially neutral of alkaline in character.

3. The surgical cement of claim 1 wherein said cementing component is selected from the group consisting of calcium sulfate-containing components, hydrates thereof and mixtures thereof, and said mixture hardens in about 20 minutes or less after said paste is formed.

4. The surgical cement of claim 1 wherein said cementing component is selected from the group consisting of calcium sulfate dihydrate, calcium sulfate hemihydrate, anhydrous calcium sulfate, calcium sulfate-calcium phosphate mixed ceramics, calcium sulfate-calcium alkali phosphate mixed ceramics and mixtures thereof.

5. The surgical cement of claim 1 wherein said cementing component is selected from the group consisting of calcium sulfate dihydrate, calcium sulfate hemihydrate, anhydrous calcium sulfate and mixtures thereof.

6. The surgical cement of claim 1 wherein said cementing component is selected from the group consisting of calcium sulfate-calcium phosphate mixed ceramics, calcium sulfate-calcium alkali phosphate mixed ceramics and mixtures thereof.

7. The surgical cement of claim 1 wherein said cementing component is selected from the group consisting of calcium sulfate-calcium alkali phosphate ceramics and mixtures thereof.

8. The surgical cement of claim 1 wherein said cementing component is combined in said mixture in the form of particles having a particle size in the range of about 3 microns to about 400 microns.

9. The surgical cement of claim 1 wherein said setting component is selected from the group consisting of citrates, tartrates, dibasic phosphate salts and mixtures thereof.

10. The surgical cement of claim 1 wherein said setting component is selected from the group consisting of citrates.

11. The surgical cement of claim 10 wherein said setting component is selected from the group consisting of ammonium citrate, alkali metal citrates, alkaline earth metal citrates, ferrous citrate, ferric citrate, ferric ammonium citrate and mixtures thereof.

12. The surgical cement of claim 10 wherein said mixture further comprises an effective amount of a strength enhancing component.

13. The surgical component of claim 12 wherein said strength enhancing component is selected from the group consisting of soluble tartrates, soluble dibasic phosphate salts, and mixtures thereof.

14. The surgical cement of claim 12 wherein strength enhancing component is selected from the group consisting of $Na_2HPO_4$, $K_2HPO_4$, $MgHPO_4$, $(NH_4)_2HPO_4$, $Na_2$ tartrate, $K_2$ tartrate, NaK tartrate, ammonium tartrate and mixtures thereof.

15. The surgical cement of claim 1 wherein said mixture further comprises a biocompatible filler component which is substantially inert with respect to the interaction between said cementing component and said setting component during said hardening.

16. The surgical cement of claim 15 wherein said biocompatible filler component is selected from the group consisting of tetracalcium phosphate, tricalcium phosphate, calcium alkali phosphate ceramic, bioglass, calcium carbonate, calcium hydroxide, calcium oxide, calcium fluoride, magnesium hydroxide, hydroxyapatite, calcium phosphorus apatite, magnesium oxide, magnesium carbonate, magnesium fluoride, collagen, other resorbable biocompatible materials and mixtures thereof.

17. The surgical cement of claim 15 wherein said biocompatible filler component is selected from the group consisting of hydroxyapatite, calcium phosphorus apatite and mixtures thereof.

18. The surgical cement of claim 15 wherein said biocompatible filler component is combined in said mixture in the form of particles having a particle size in the range of about 3 microns to about 400 microns.

19. The surgical element of claim 1 further comprises an antibiotic component.

20. The surgical cement of claim 1 further comprises a bone growth protein component.

* * * * *